United States Patent
Ogdahl et al.

(10) Patent No.: US 9,877,717 B2
(45) Date of Patent: Jan. 30, 2018

(54) CONNECTOR FOR MESH SUPPORT INSERTION

(75) Inventors: Jason Westrum Ogdahl, Minneapolis, MN (US); John F. Otte, St. Anthony, MN (US); Mark S. Bouchier, Lakeville, MN (US); Brian P. Watschke, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 269 days.

(21) Appl. No.: 13/034,842

(22) Filed: Feb. 25, 2011

(65) Prior Publication Data

US 2011/0144418 A1  Jun. 16, 2011

Related U.S. Application Data

(63) Continuation of application No. 11/537,891, filed on Oct. 2, 2006, now Pat. No. 7,909,753.

(60) Provisional application No. 60/724,332, filed on Oct. 5, 2005.

(51) Int. Cl.
| | | |
|---|---|---|
| *A61F 2/00* | (2006.01) | |
| *A61B 17/06* | (2006.01) | |
| *A61B 17/00* | (2006.01) | |

(52) U.S. Cl.
CPC ............ *A61B 17/06109* (2013.01); *A61B 2017/00805* (2013.01); *A61B 2017/06009* (2013.01); *A61B 2017/06042* (2013.01); *A61F 2/0045* (2013.01)

(58) Field of Classification Search
CPC .. A61F 2/00–2/0095; A61F 2002/0072; A61F 2002/0823; A61F 2002/0829; A61F 2002/0835

USPC .............. 600/29–31, 37; 606/151–158
See application file for complete search history.

(56) References Cited

U.S. PATENT DOCUMENTS

| | | | |
|---|---|---|---|
| 4,683,883 A | * | 8/1987 | Martin .................. A61F 2/2427 606/1 |
| 6,884,212 B2 | | 4/2005 | Thierfelder et al. |
| 6,911,003 B2 | | 6/2005 | Anderson et al. |
| 7,025,772 B2 | | 4/2006 | Gellman et al. |
| 7,407,480 B2 | | 8/2008 | Staskin et al. |
| 7,909,753 B1 | | 3/2011 | Ogdahl et al. |
| 2002/0099259 A1 | * | 7/2002 | Anderson et al. .............. 600/29 |
| 2003/0023138 A1 | | 1/2003 | Luscombe |

(Continued)

FOREIGN PATENT DOCUMENTS

| | | |
|---|---|---|
| WO | WO2007149593 | 12/2007 |
| WO | WO2010093421 | 8/2010 |

*Primary Examiner* — Catherine B Kuhlman
(74) *Attorney, Agent, or Firm* — Brake Hughes Bellermann LLP

(57) ABSTRACT

Disclosed is a surgical system for positioning an implant in a patient. The surgical system includes an insertion needle and a connector. The insertion needle has a distal end with a channel formed therein. The channel has a first end and a second end. The first end extends to the distal end. The second is laterally offset from the first end and does not extend to the distal end. The connector has a first end and a second end. The first end is attached to the implant that is to be positioned in the patient. The second end has a recess formed therein. The recess generally conforms to the distal end of the insertion needle. The connector has an inwardly directed extension that extends into the recess. The inwardly directed extension engages the insertion needle through the channel.

9 Claims, 8 Drawing Sheets

(56) References Cited

U.S. PATENT DOCUMENTS

| | | |
|---|---|---|
| 2003/0036676 A1 | 2/2003 | Scetbon |
| 2003/0171644 A1* | 9/2003 | Anderson et al. .............. 600/29 |
| 2003/0212305 A1 | 11/2003 | Anderson et al. |
| 2004/0087970 A1* | 5/2004 | Chu et al. .................... 606/119 |
| 2005/0256366 A1 | 11/2005 | Chu |
| 2006/0089525 A1* | 4/2006 | Mamo et al. ................... 600/37 |
| 2008/0103351 A1 | 5/2008 | Staskin et al. |
| 2008/0140218 A1 | 6/2008 | Staskin et al. |
| 2008/0207989 A1 | 8/2008 | Kaleta et al. |
| 2009/0012592 A1 | 1/2009 | Ogdahl et al. |
| 2009/0240104 A1 | 9/2009 | Ogdahl et al. |
| 2010/0105979 A1 | 4/2010 | Otte et al. |
| 2010/0256442 A1 | 10/2010 | Ogdahl et al. |
| 2011/0034759 A1 | 2/2011 | Ogdahl et al. |

* cited by examiner

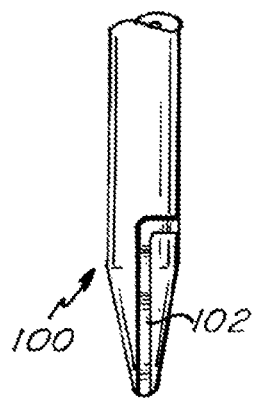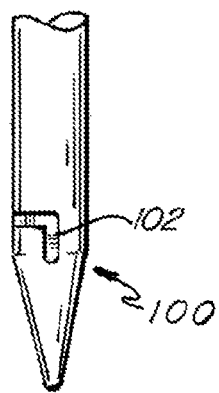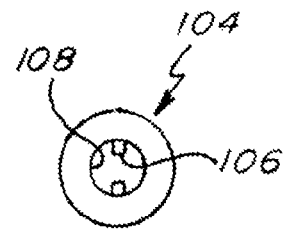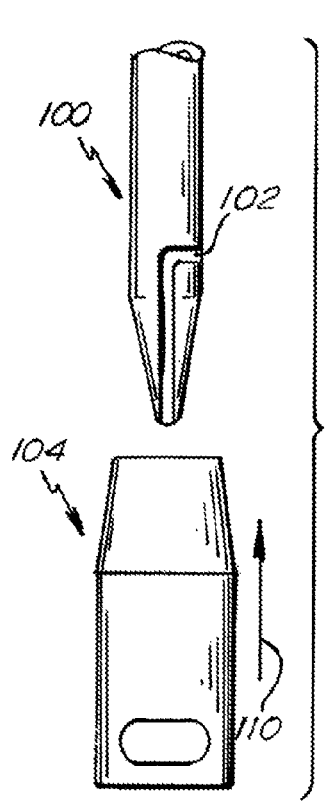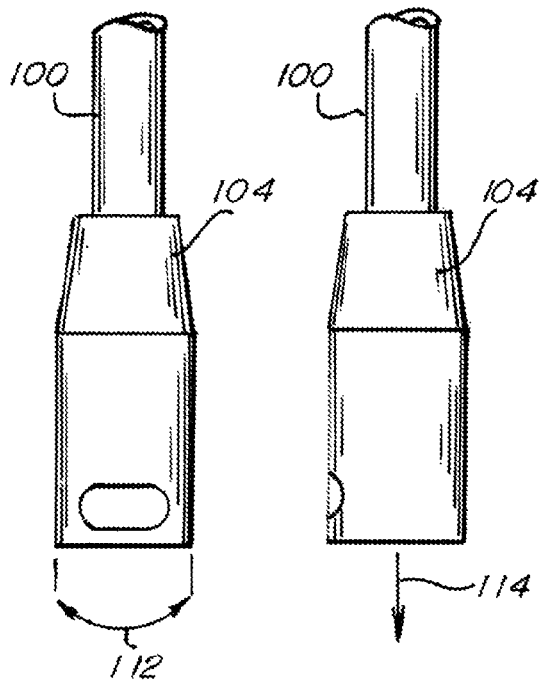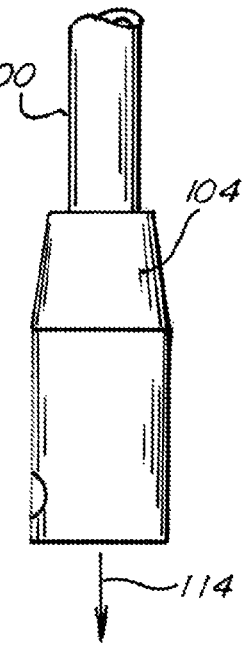

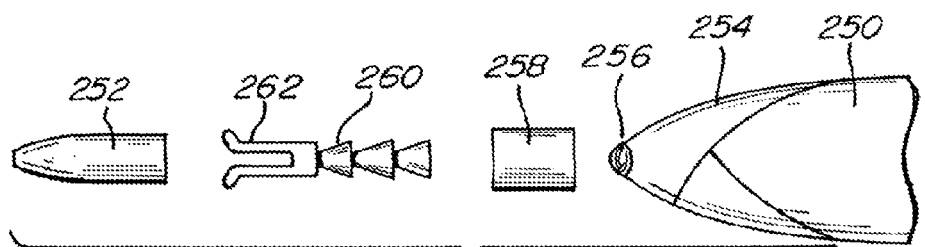
*Fig.26.*
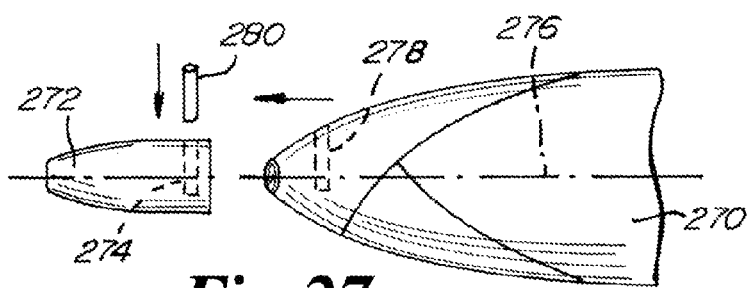
*Fig.27.*
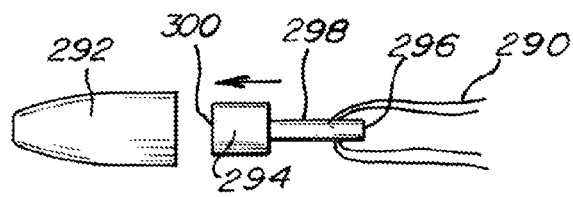
*Fig.28.*
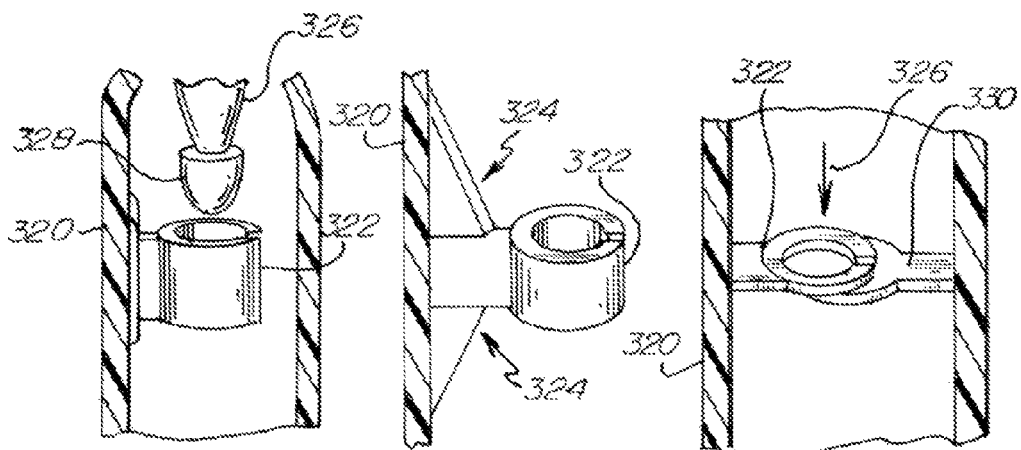
*Fig.29.*   *Fig.30.*   *Fig.31.*

CONNECTOR FOR MESH SUPPORT INSERTION

This application is a Continuation Application of U.S. patent application Ser. No. 11/537,891, filed Oct. 2, 2006, which claims the benefit of and priority to U.S. Provisional Application No. 60/724,332, filed Oct. 5, 2005, with each of the above-referenced Applications incorporated herein by reference in their entirety.

FIELD OF THE INVENTION

The invention relates generally to treatments for providing anatomical support within the human pelvis. More particularly, the invention relates to devices and surgical techniques for treating incontinence through use of an anatomical support.

BACKGROUND OF THE INVENTION

There are various surgical techniques that use mesh or other devices to support portions of a patient's body such as bladder or uterus, for example those described in U.S. Pat. Nos. 6,911,003 and 6,884,212, which are hereby incorporated by reference. While it is possible to make a relatively large incision to provide the surgeon with direct access to the area in which the mesh support structure is being placed, this technique is undesirable because it not only increases the potential of complications but also increases the time for the patient to recover from the surgery.

As such, it is desirable to make relatively small incisions in the patient and then feed the mesh support structure to desired locations using needles or other devices. There are several challenges associated with using needles to position the mesh support structure. The most significant challenge relates to attaching the mesh support structure to the needle so that the mesh support structure can be readily moved inside of the patient.

One technique used by the assignee of the present application to attach insertion needles to mesh support structures is through a snapping connection. Such a connection requires a relatively large force (at least 10 pounds) to disconnect the insertion needle from the mesh support structure to ensure that the mesh support structure does not inadvertently detach from the insertion needle during the insertion of the mesh support structure.

SUMMARY OF THE INVENTION

The invention is directed to a surgical system for positioning an implant in a patient. The surgical system includes an insertion needle and a connector. The insertion needle has a distal end with a channel formed therein. The channel has a first end and a second end. The first end extends to the distal end. The second is laterally offset from the first end and does not extend to the distal end.

The connector has a first end and a second end. The first end is attached to the implant that is to be positioned in the patient. The second end has a recess formed therein. The recess generally conforms to the distal end of the insertion needle. The connector has an inwardly directed extension that extends into the recess. The inwardly directed extension engages the insertion needle through the channel.

Another embodiment of the invention is directed to a surgical system for positioning an implant in a patient. The surgical system includes an insertion needle, a connector and a removal tool. The insertion needle has a tip extending therefrom. The insertion needle has a reduced diameter section proximate the tip.

The connector has a recess formed therein that is adapted to receive at least a portion of the insertion needle. The connector includes a resilient leg mounted thereto adjacent the recess. The leg engages the insertion needle proximate the tip to retain the insertion needle in the connector. The removal tool is capable of engaging the leg to urge the leg to a release position that permits the connector to be separated from the insertion needle.

Still another embodiment of the invention is directed to a surgical system for positioning an implant in a patient. The surgical system includes an insertion needle, a connector and a collar. The insertion needle has a tip extending therefrom. The insertion needle has a reduced diameter section proximate the tip.

The connector has a central aperture formed therein that is adapted to receive at least a portion of the insertion needle. The connector includes a resilient leg mounted thereto adjacent the recess. The leg engages the insertion needle proximate the tip to retain the insertion needle in the connector.

The collar has a recess formed therein. The collar is mountable on the reduced diameter section to urge the leg away from the reduced diameter section to release the connector from the insertion needle.

Yet another embodiment of the invention is directed to a surgical system for positioning an implant in a patient. The surgical system includes an insertion needle and a connector. The insertion needle has a tip extending therefrom. The insertion needle has a reduced diameter section proximate the tip.

The connector has a recess formed therein that is adapted to receive at least a portion of the insertion needle. The connector includes a resilient leg mounted thereto adjacent the recess. The leg engages the insertion needle proximate the tip to retain the insertion needle in the connector. The connector has a slit formed therein proximate the leg.

Another embodiment of the invention is directed to a surgical system for positioning an implant in a patient. The surgical system includes an insertion needle and a connector. The insertion needle has a tip extending therefrom. The insertion needle has a reduced diameter section proximate the tip.

The connector has a recess formed therein that is adapted to receive at least a portion of the insertion needle. The connector includes a C-shaped leg assembly mounted proximate the recess. The C-shaped leg assembly has an aperture formed therein that is adapted to receive at least a portion of the insertion needle.

Still another embodiment of the invention is directed to a surgical system for positioning an implant in a patient. The surgical system includes an insertion needle and a connector. The insertion needle has a tip extending therefrom. The insertion needle has a reduced diameter section proximate the tip.

The connector has a recess formed therein that is adapted to receive at least a portion of the insertion needle. The connector includes a first extension and a second extension. An end of the first extension extends beyond an end of the second extension. The first extension and the second extension define an aperture therebetween that is adapted to receive at least a portion of the insertion needle.

BRIEF DESCRIPTION OF THE DRAWINGS

FIG. 1 is a front view of a J-shaped slot formed in an insertion needle.

FIG. 2 is a side view of the insertion needle from FIG. 1.

FIG. 3 is an end view of the insertion needle from FIG. 1.

FIG. 4 is an end view of a connector for use with the insertion needle of FIG. 1.

FIG. 5 is a side view illustrating movement of the connector towards the insertion needle.

FIG. 6 is a side view illustrating rotating the connector with respect to the insertion needle.

FIG. 7 is a side view illustrating moving the connector away from the insertion needle.

FIG. 26 is side view of an alternate mechanism for attaching the connector to the mesh assembly with a barb and collar configuration.

FIG. 27 is a side view of an alternate configuration for attaching the connector to the mesh assembly with a pin.

FIG. 28 is a side view of an alternative configuration for attaching the connector to the mesh assembly with an adaptor.

FIG. 29 is a perspective view of a C-shaped leg extending from an inner wall of the connector.

FIG. 30 is a perspective view of the C-shaped leg with reinforcing ribs.

FIG. 31 is a perspective view of a support shelf used in conjunction with the C-shaped leg.

DETAILED DESCRIPTION OF THE PREFERRED EMBODIMENTS

Figure 8:
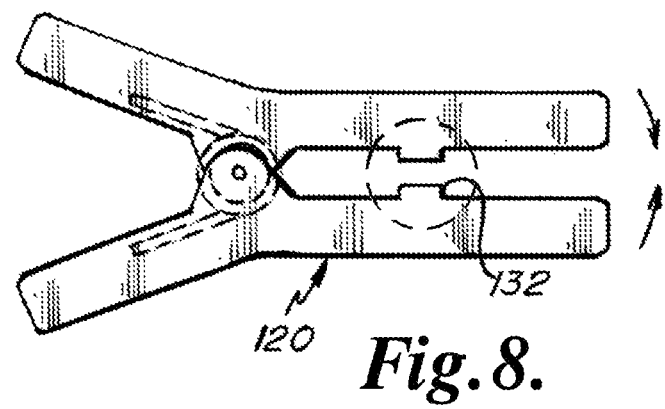
FIG. 8 is a side view of a tool for detaching the connector from the insertion needle.

The invention is directed to several devices and techniques for use in positioning mesh within a patient (male or female) that are discussed in more detail below.

A conventional technique used for treatment of vaginal wall prolapse is with a mesh support structure having four legs extending therefrom. To reduce the risks of contamination, this surgical procedure is performed using a kit that not only includes the mesh support structure but also four insertion needles that are used for positioning the mesh support structure within the patient. Similar kits have also been used to treat urinary stress incontinence.

To substantially reduce the potential of the insertion needle detaching from the mesh as the mesh is positioned in the patient, a prior technique for attaching the insertion needle to the mesh utilizes a snapping or locking mechanism. The friction fit mechanism typically requires a relatively large lineal force of greater than 10 pounds to detach the insertion needle from the mesh support structure.

Because this embodiment of the invention enables the needle to be readily detached from the connector, this embodiment enables a mesh support structure having four legs to be inserted using two insertion needles. The insertion needles used in this embodiment may be identified as right and left.

The insertion needles each include a connector that enables the insertion needles to be readily detached from the mesh support structure. Each of the insertion needles is used with a connector that allows for quick detachment from the mesh support structure either through a quick detachment geometry built into the insertion needle or the connector, or through the use of a tool that aides in the quick removal of the connector from the insertion needle.

In one configuration of the needle, the needle 100 includes at least one J-shaped slot 102 formed therein, as illustrated in FIGS. 1-3. The connector 104 includes an inwardly directed extension 106 that extends from a wall of the aperture 108 through which the needle 100 is inserted, as illustrated in FIG. 4. The inwardly directed extension 106 has a width that is slightly smaller than a width of the J-shaped slot 102.

When connecting the connector 104 to the insertion needle 100, the connector 104 is moved towards the insertion needle 100, as illustrated by arrow 110 in FIG. 5, until the insertion needle 100 extends into the connector 104. As the insertion needle 100 is inserted into the connector 104, the inwardly directed extension 106 slides in the J-shaped slot 102 until the inwardly directed extension 106 contacts the bottom of the J-shaped slot 102. At that time, the connector 104 is rotated with respect to the insertion needle 100, as illustrated by arrow 112 in FIG. 6. The connector 104 is then pulled away from the insertion needle 100, as illustrated by arrow 114 in FIG. 7.

The connector 104 is thereby attached to the insertion needle 100 such that lineal pulling and pushing of the insertion needle 100 enables the connector 104 and the attached portion of the mesh support structure to be pulled through the patient. Once the mesh support structure is pulled to a desired location, the attachment process set forth above is reversed to detach the connector 104 from the insertion needle 100.

Figure 9:
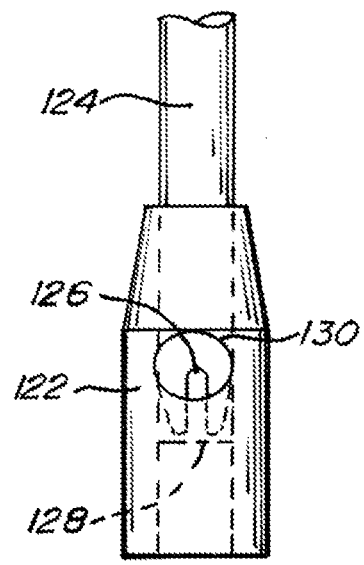
FIG. 9 is a side view of the connector for use with the tool of FIG. 8.

In another configuration of the connector, a tool 120, illustrated in FIG. 8, is provided to detach the connector 122 from the insertion needle 124. At least one leg 126 is provided on an inner surface of the connector 122, as illustrated in FIG. 9. As the insertion needle 124 is inserted into the connector 122, the leg 126 engages a ridge 128 extending from the insertion needle 124 and thereby retains the connector 122 on the insertion needle 124. The legs 126 may be positioned on opposite sides of the connector 122 such that pushing opposite legs 126 towards each other enables the connector 122 to be released from the insertion needle 124.

Each leg 126 may be positioned proximate an opening 130 that extends through a wall of the connector 122. Each opening 130 is adapted to receive a tab 132 on a pliers-like tool 120. When the tab 132 engages the leg 126, the connector 122 may be removed from the needle 124.

Using this system, the right and left insertion needles are inserted into the patient using conventionally known techniques. The right and left insertion needles are then connected to two of the legs extending from the mesh support structure and the insertion needles are withdrawn from the patient to pull each of the legs through the associated obturator. Each of the connectors is then disengaged to separate the insertion needles from the mesh support structure, the process is then repeated to insert the other two legs into the desired location in the patient.

Figure 10:
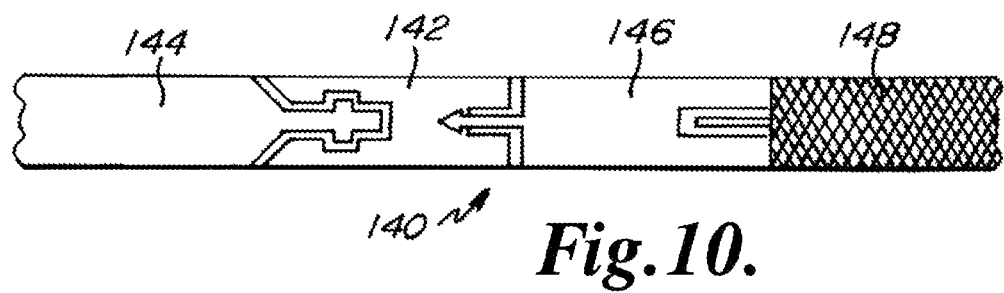
FIG. 10 is a sectional view of a two-piece connector attaching a mesh support structure.

As an alternative to using a one-piece connector that is discussed above, it is also possible to use a two-piece connector 140, as illustrated in FIG. 10. In the two piece connector 140, a proximal connector portion 142 is attached to the insertion needle 144 and a distal connector portion 146 is attached to the mesh support structure 148. The proximal connector portion 142 and the distal connector portion 144 engage each other to attach the insertion needle to the connector 140 such as by using one of the connection methods described herein.

Figure 11:
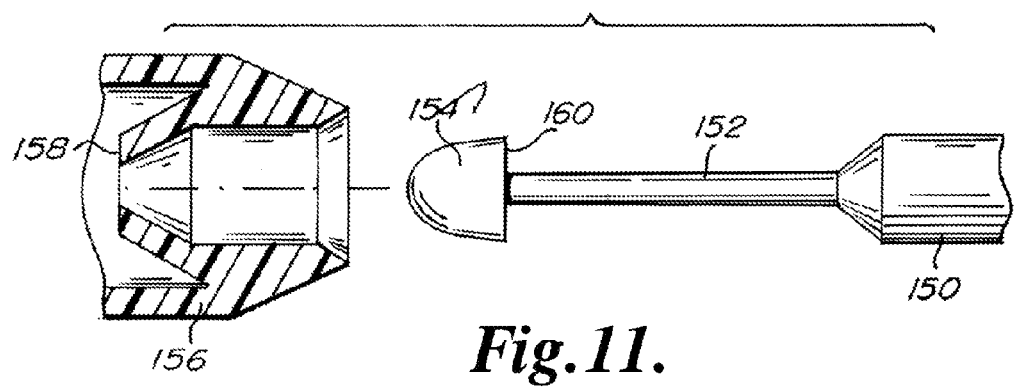
FIG. 11 is a sectional view of a needle in proximity to the connector.

Another configuration for removably attaching the connector to the needle includes an insertion needle 150 with a reduced diameter section 152 that is adjacent to but offset from a tip 154 of the insertion needle 150, as illustrated in FIG. 11. The reduced diameter section 152 may have a length of about 0.75 inches. The connector 156 includes at least one inwardly directed tab 158 that engages a lip 160 where the reduced diameter section 152 and the tip 154 intersect to retain the connector 156 on the insertion needle 150.

Figure 12:
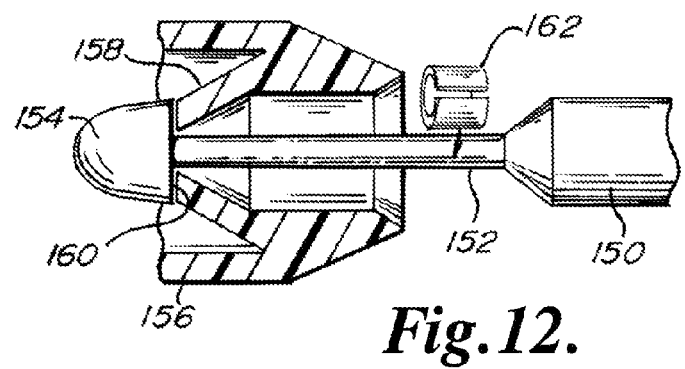
FIG. 12 is a sectional view of a collar being placed on the insertion needle.

When it is desired to remove the connector 156 from the insertion needle 150, a C-shaped collar 162 is placed over the reduced diameter section 152, as illustrated in FIG. 12. The collar 162 is formed with a length based upon the length of the reduced diameter section 152 and the distance to the tab 158 from the front of the connector 156.

Figure 13:
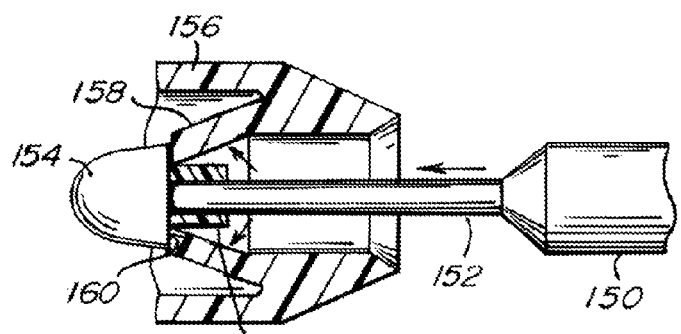
FIG. 13 is a sectional view of the collar dislodging the connector from the insertion needle.

The collar 162 is then urged towards the tip 154, as illustrated in FIG. 13. The collar 162 thereby contacts the at least one inwardly directed tab 158 and urges the inwardly directed tab 158 outward. When this occurs, the inwardly directed tab 158 no longer engages the lip 160, which allows the connector 156 to be removed from the insertion needle 150. The collar 162 may be removed from the reduced diameter section 152 and the insertion needle 150 may be reused. Alternatively, the collar 162 may be permanently left on the insertion needle 150.

Figure 14:
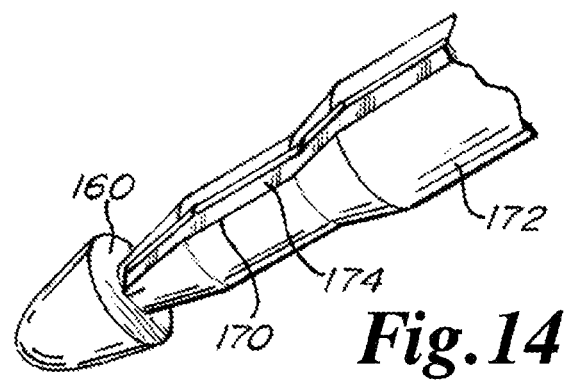
FIG. 14 is a side view of an insertion needle having a channel formed therein.

Alternatively, a channel 170 may be formed in the insertion needle 172, as illustrated in FIG. 14. The channel 170 would receive an arm 174 or other device that extends to proximate the lip 160. The arm 174 may be pivoted to urge the inwardly directed tab outward.

Figure 15:
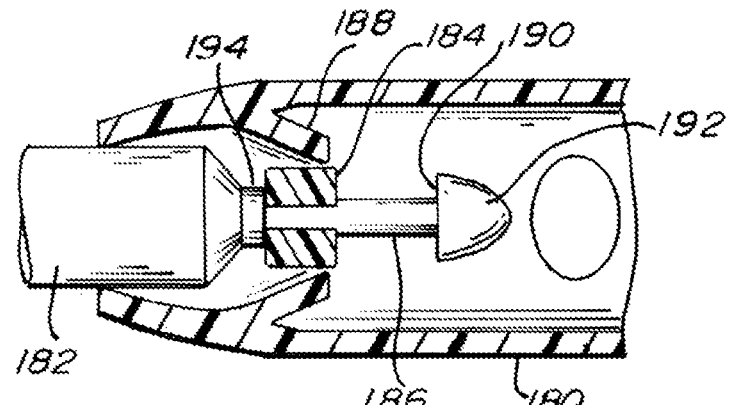
FIG. 15 is a sectional view of connector legs on the collar.
Figure 16:
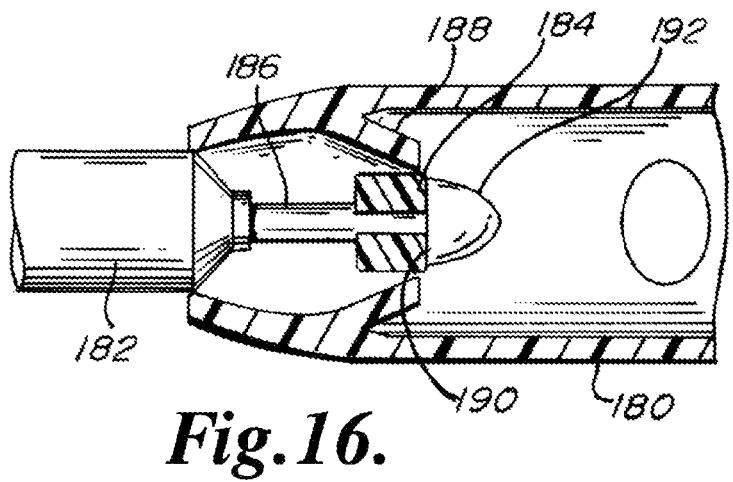
FIG. 16 is a sectional view of the collar moved against the tip of the insertion needle.
Figure 17:
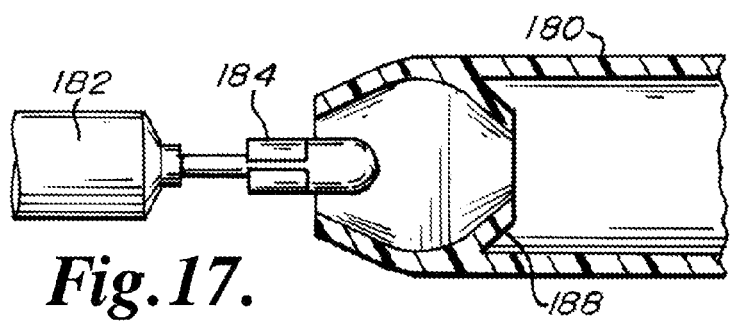
FIG. 17 is a sectional view of the connector disengaged from the insertion needle.

In yet another configuration of the removable connector, a pump action mechanism is provided to detach the connector 180 from the insertion needle 182, as illustrated in FIGS. 15-17. Using this mechanism, the collar 184 is formed with a length that may be less than a length of the reduced diameter region 186. This configuration enables the collar 184 to slide with respect to the insertion needle 182.

When the connector 180 is initially attached to the insertion needle 182, the connector arms 188 engage a lip 190 where the tip 192 and the reduced diameter region 186 intersect. When it is desired to remove the connector 180 from the insertion needle 182, the connector 180 is urged away from the distal end of the insertion needle 182, as illustrated in FIG. 15.

Sliding of the collar 184 away from the distal end of the insertion needle 182 is limited by a stop 194 provided at a proximal end of the reduced diameter region 186. This movement causes the connector arms 188 to be positioned over the collar 184, as illustrated in FIG. 15.

Thereafter, the connector 180 is moved away from the insertion needle 182. The lip 190 limits movement of the collar 184, as illustrated in FIG. 16. The continued pulling of the connector 180 away from the insertion needle 182 causes the connector arms 188 to move past the lip 190 to release the connector 180 from the insertion needle 182, as illustrated in FIG. 17.

Figure 18:
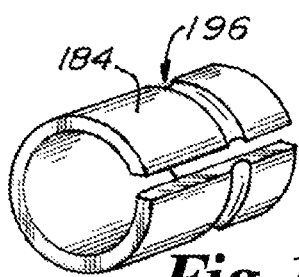
FIG. 18 is a perspective view of an alternative configuration of the collar having an indent formed therein.
Figure 19:
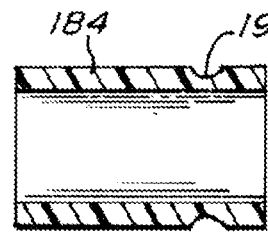
FIG. 19 is a sectional view of the collar of FIG. 18.
Figure 20:
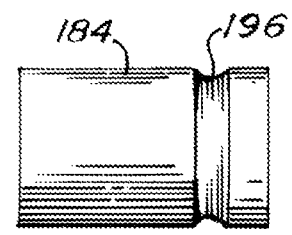
FIG. 20 is a side view of the collar of FIG. 18.

The collar 184 may include a ridge 196 or indent on an outer surface thereof, as illustrated in FIGS. 18-20, to assist in the connector arms 188 retaining the collar 184 during movement.

Figure 21:
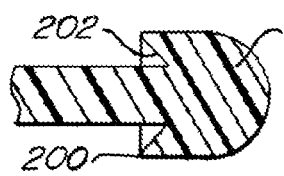
FIG. 21 is a sectional view of an alternative tip configuration.
Figure 22:
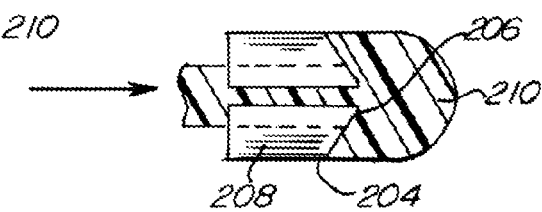
FIG. 22 is a sectional view of a collar engaging the alternative tip configuration of FIG. 21.

A lip 200 may also include an angled surface 202 that forms a pocket, as illustrated in FIGS. 21-22. The angled surface 202 may substantially correspond with an angled surface 204 on a distal end 206 of the collar 208. This configuration of the insertion needle 210 and collar 208 enhances the ability to provide a smooth transition between the collar 208 and the lip 200 even if they are not in exact alignment.

Figure 23:
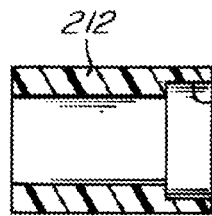
FIG. 23 is a sectional view of another configuration of the collar with a lip formed therein.
Figure 24:
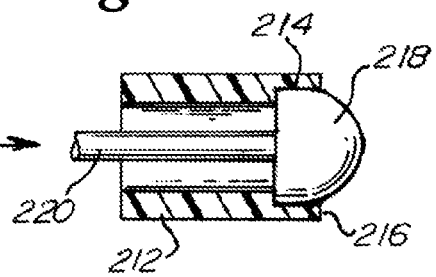
FIG. 24 is a sectional view of the collar of FIG. 23 adjacent to an insertion needle tip.

Yet another configuration of the collar 212 includes a lip 214 proximate a distal end 216 thereof, as illustrated in FIGS. 23-24. The lip 214 extends over a portion of the tip 218 when the connector is being removed from the insertion needle 220 to enhance the ability to remove the connector from the insertion needle 220.

Figure 25:
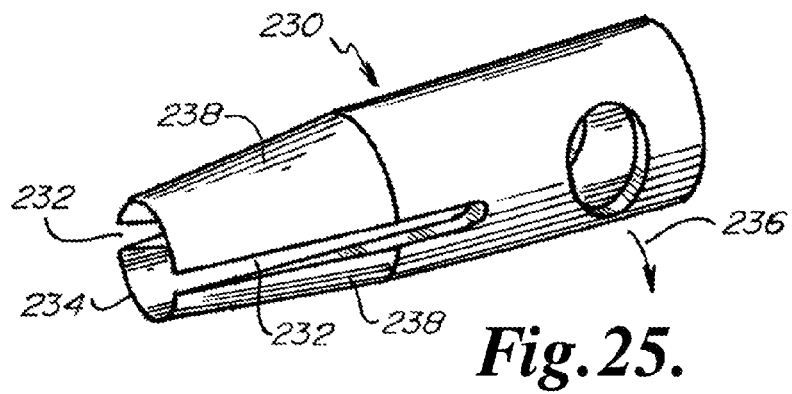
FIG. 25 is a perspective view of an alternative connector having a pair of slots formed therein.

Another configuration of the connector 230 has at least one slit 232 in the distal end 234 thereof, as illustrated in FIG. 25. Once the insertion needle (not shown) is inserted into the connector 230, legs (not shown) engage a lip near the tip of the needle to retain the connector 230 on the insertion needle in response to lineal movement of the needle towards and away from the connector 230. Alternatively, it is possible to form the connector 230 from a flexible material that provides a performance that is similar to the slit 232

When it is desired to remove the connector 230 from the insertion needle, the connector 230 is pivoted with respect to the insertion needle, as indicated by arrow 236. At least one slit 232 enables sides 238 of the connector 230 to be urged apart from each other, which thereby releases the connector 230 from the insertion needle.

Concerns when feeding mesh through a patient are minimizing a profile of the region proximate the interconnection between the needle and the mesh and providing a smooth outer surface.

Instead of feeding the mesh assembly through a hole in the side of the connector, the above concerns may be addressed by attaching the mesh assembly to a proximal end of the connector.

As an initial step in attaching the mesh assembly 250 to the connector 252, an outer sheath 254 on the mesh assembly 250 is rolled so that a distal end 256 of the sheath 254 is generally tubular, as illustrated in FIG. 26. The distal end 256 of the sheath 254 is extended through a collar 258 and a barbed adaptor 260 is inserted into the sheath 254.

The collar 258 is moved over the barbed adaptor 260 to retain the adaptor 260 in a fixed position with respect to the mesh assembly 250. The adaptor 260 may be then secured to the connector 252 using a snap feature 262.

An alternative technique for attaching a mesh assembly 270 to a connector 272 includes an aperture 274 in the connector 272 that is oriented substantially transverse to a central axis 276 of the connector 272, as illustrated in FIG. 27. A corresponding aperture 278 would be formed in the mesh assembly 270.

The mesh assembly 270 is inserted into the proximal end of the connector 272 until the aperture 274 in the connector 272 is generally aligned with the aperture 278 in the mesh assembly 270. A pin 280 is then inserted through the connector and mesh assembly apertures 274, 278 to retain the connector 272 and mesh assembly 270 in a fixed position with respect to each other.

Another technique for attaching a mesh assembly 290 to a connector 292 would be through the use of an adaptor 294, as illustrated in FIG. 28. A proximal end 296 of the adaptor 294 has an eyelet 298 extending therethrough that is adapted to receive the mesh assembly 290.

A distal end 300 of the adapter 294 is then attached to the connector 292 such as through welding or a snap feature. Alternatively, the distal end 300 of the adapter 294 may have a threaded outer surface. The threaded outer surface would engage a threaded inner surface in the connector 292 to removably attach the mesh assembly 290 to the connector 292.

As an alternative to providing at least one leg on the connector for attaching the connector to the needle, the connector 320 may include a C-shaped connector 322 that extends inwardly from a wall thereof, as illustrated in FIG. 29. To compensate for the force applied to the C-shaped connector 322 as the connector 320 is attached to an insertion needle 326 or as the assembly is pulled through the tissue, one or more ribs 324 may extend from the C-shaped connector 322 to the wall of the connector 320, as illustrated in FIG. 30.

As the insertion needle 326 is inserted into the C-shaped connector 322, the walls of the C-shaped connector 322 are urged apart from each other to allow the needle 326 to pass therethrough. Once the tip of the needle 326 passes the C-shaped connector 322, the C-shaped connector 322 engages the lip 328 and thereby prevents the connector 320 from being removed from the insertion needle 326.

Another technique to reduce the potential of the C-shaped connector 322 being damaged during insertion of the needle 326 into the connector 320 is through a support shelf 330 that extends from an opposite wall of the connector 320, as illustrated in FIG. 31. Forces generated during the insertion of the needle 326 into the connector 320 would thereby be distributed over both the C-shaped connector 322 and the support shelf 330.

Figure 32:
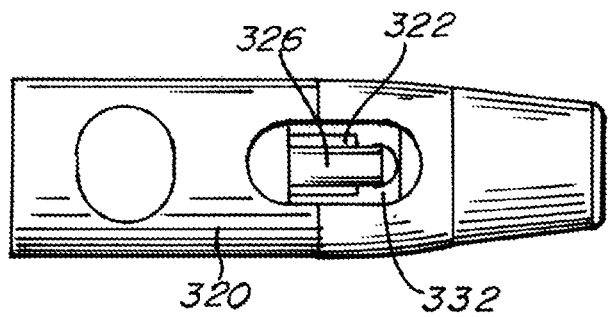
FIG. 32 is a side view of the connector showing an aperture formed therein.
Figure 33:
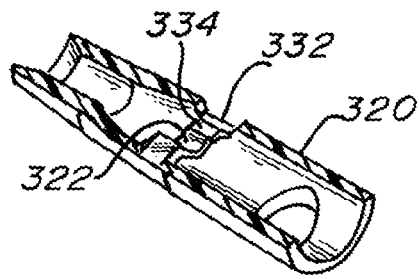
FIG. 33 is a perspective sectional view of another configuration of the connector.

The wall of the connector 320 above an open end of the C-shaped connector 322 may have an aperture 332 formed therein, as illustrated in FIGS. 32-33. When it is desired to separate the connector 320 from the insertion needle 326, a tool (not shown) having a thin blade such as a screwdriver is inserted into the aperture 332 to cause the legs of the C-shaped connector 322 to more apart from each other to thereby release the needle 326.

Figure 34:
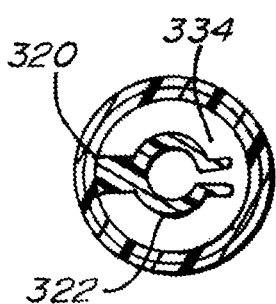
FIG. 34 is a sectional view of the connector of FIG. 33.

To further enhance the ability to move apart the arms of the C-shaped connector 322, an extension 334 may be provided on the end of the C-shaped connector 322 to increase the surface areas that the tool contacts, as illustrated in FIGS. 33-34.

Figure 35:
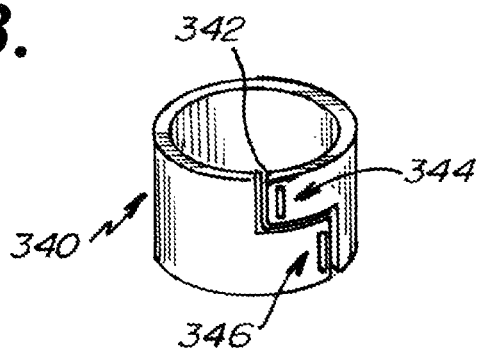
FIG. 35 is a perspective view of an alternate configuration for the C-shaped leg.
Figure 36:
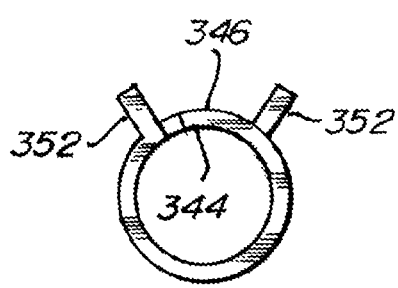
FIG. 36 is top view of the C-shaped leg of FIG. 35.

As an alternate to the embodiment discussed with respect to FIGS. 29-34, it is also possible to form a locking mechanism 340 to be removed using a squeezing motion. In one configuration, the locking mechanism 340 may have a generally circular shape having an opening 342 at one side thereof, as illustrated in FIGS. 35-36.

To facilitate attaching and detaching the locking mechanism 340, a first extension 344 and a second extension 346 extend from opposite ends of the locking mechanism 340. An end of the first extension 344 extends beyond an end of the second extension 346.

Figure 37:
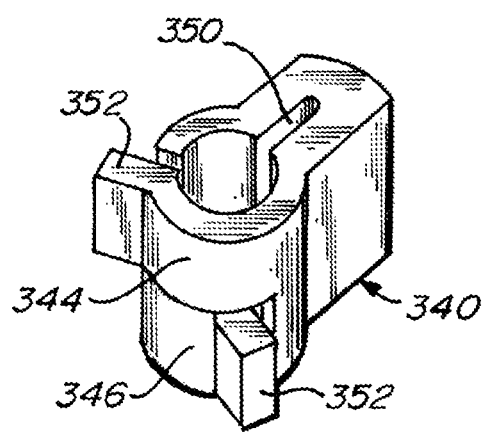
FIG. 37 is a perspective view of the C-shaped leg of FIG. 35 with a slot formed between the legs thereof.

Depending upon the material from which the locking mechanism 340 is formed, it may be necessary to increase the flexibility of the first and second extensions 344, 346 by providing a slot 350 therebetween, as illustrated in FIG. 37. A person of skill in the art will appreciate that the deeper the slot 350, the more flexibility that is imparted to the first and second extensions 344, 346.

Figure 38:
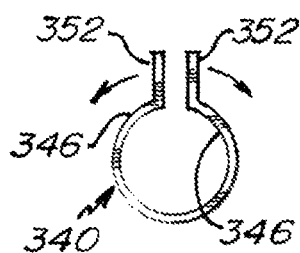
FIG. 38 is a top view of the C-shaped leg of FIG. 37 in a wide opened configuration.
Figure 39:
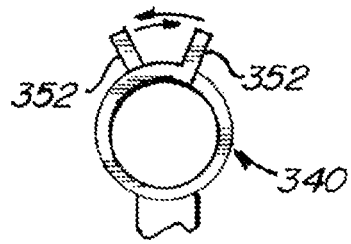
FIG. 39 is a top view of the C-shaped leg of FIG. 37 in a relaxed configuration.
Figure 40:
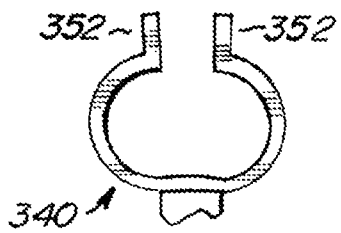
FIG. 40 is a top view of the C-shaped leg of FIG. 37 in an expanded configuration.

The first extension 344 and the second extension 346 may each have a tab 352 extending outwardly therefrom proximate an end thereof. Since the first extension 344 is offset from the second extension 346, urging the tabs 352 towards each other causes a diameter of the locking mechanism 340 to increase and thereby allows the locking mechanism 340 to release the needle (not shown). When removing the locking mechanism 340, it may be necessary to urge the tabs 352 pas Compared to conventional tabs that do not overlap, moving the tabs 352 the same distance requires a smaller net space, which translates into a smaller window in the connector sidewall. The net space is smaller because the travel of the tabs overlap each other, as illustrated in FIGS. 38-40.

Figure 41:
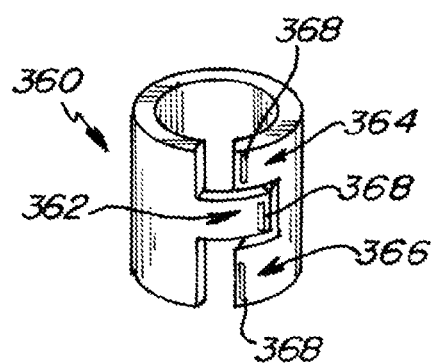
FIG. 41 is a perspective view of an alternate configuration of the C-shaped leg.

In an alternative configuration of the locking mechanism 340, a locking mechanism 360, which is illustrated in FIG. 41, includes a central extension 362 that is positioned between an upper extension 364 and a lower extension 366. Ends of the upper and lower extension 364, 366 extend beyond an end of the central extension 362.

The central, upper and lower extensions 362, 364, 366 each have a tab 368 extending outwardly therefrom proximate an end thereof. Since the central extension 362 is offset from the upper and lower extensions 364, 366, urging the tab 368 on the central extension 362 towards the tabs 368 on the upper and lower extensions 364, 366 causes a diameter of the locking mechanism 360 to increase and thereby allows the locking mechanism 360 to release the needle (not shown).

Because the central extension 362 is located between the upper and lower extensions 364, 366, this configuration of the locking mechanism 360 has greater symmetry than the embodiment of the locking mechanism disclosed in FIG. 35 and thereby may reduce twisting of the locking mechanism 360 during operation.

A technique for attaching the mesh assembly to the connector is directed to molding the connector over an end of the mesh assembly, such as for use with the connector illustrated in FIGS. 27-29. The connector mold is formed with an opening that is adapted to receive the end of the mesh assembly. As an alternative to molding the entire connector over the end of the mesh assembly, the invention relates to molding a connector over the end of the mesh assembly and then attaching the connector to the connector.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A surgical system for positioning an implant in a patient, comprising:
an elongate sling implant having a support portion and first and second end portions;
a distal connector having an outer diameter and a proximate engagement end;
a sling connector including;
a barbed element having a first end and a second end, the barbed element having a plurality of cone-shaped barbs provided in an end-to-end alignment, with each of the plurality of cone-shaped barbs having an overall length and including an angled outer surface extending substantially and contiguously along the entirety of the overall length, the first end of the barbed element configured to be coupled to the first end portion of the elongate sling implant;
a collar having a lumen configured to receive at least a portion of the barbed element;
a snap feature having a longitudinal axis and spaced apart extending elements, the snap feature having a first end and a second end, the first end of the snap feature extending from the second end of the barbed element, the extending elements extending out along the longitudinal axis with an elongate and generally U-shaped channel defined therebetween and each extending element having an angled portion extending away from the longitudinal axis, with the barbed element and the snap feature provided in an end-to-end alignment,
the extending elements configured to engage with the proximate engagement end of the distal connector.

2. The surgical system of claim 1, further including an insertion needle having a distal tip.

3. The surgical system of claim 1, wherein the elongate sling implant is constructed of a mesh material.

4. The surgical system of claim 1, further including a second sling connector provided at the second end portion of the elongate sling implant.

5. A surgical system for positioning an implant in a patient to treat incontinence, comprising:
an insertion needle having a tip extending therefrom;
an elongate mesh sling implant;
a sling connector having:
an adaptor having a first end and a second end, the adaptor having a plurality of cone-shaped barbed elements provided in an end-to-end alignment, with each of the plurality of cone-shaped barbs having an overall length and including a tapered outer surface extending substantially and contiguously along the entirety of the overall length;
a collar having a lumen configured to receive at least a portion of the adaptor; and
a pronged snap feature having a longitudinal axis and having members extending away from the longitudinal axis with an elongate and generally U-shaped channel defined between the members, the pronged snap feature having a first end and a second end, the first end of the snap feature extending from the second end of the adaptor, the plurality of cone-shaped barbed elements and the pronged snap feature provided in an end-to-end orientation; and
a distal connector having an outer diameter, a proximate engagement end, and adapted to operatively receive the pronged snap feature, and wherein the tip of the insertion needle is adapted to engage with the distal connector to facilitate passage of the distal connector through tissue within the patient.

6. The surgical system of claim 5, wherein at least a portion of the distal connector is cylindrical.

7. The surgical system of claim 5, further including a second sling connector provided at a second end portion of the elongate sling implant.

8. The surgical system of claim 5, wherein the tip of the insertion needle has a reduced diameter relative to a body portion of the insertion needle.

9. The surgical system of claim 5, wherein the sling connector is removably provided at an end portion of the sling implant.

* * * * *